United States Patent [19]

Yamada et al.

[11] Patent Number: 5,304,377
[45] Date of Patent: Apr. 19, 1994

[54] PROLONGED RELEASE PREPARATION AND POLYMERS THEREOF

[75] Inventors: Minoru Yamada; Seiko Ishiguro, both of Kawanishi; Yasuaki Ogawa, Otokuni, all of Japan

[73] Assignee: Takeda Chemical Industries, Ltd., Osaka, Japan

[21] Appl. No.: 986,299

[22] Filed: Dec. 7, 1992

Related U.S. Application Data

[63] Continuation of Ser. No. 777,170, Oct. 16, 1991, abandoned.

[30] Foreign Application Priority Data

Oct. 16, 1990 [JP] Japan .................. 2-278037
Aug. 28, 1991 [JP] Japan .................. 3-217045

[51] Int. Cl.$^5$ .................. A61K 9/22; A61K 9/52; A61K 31/74
[52] U.S. Cl. .................. 424/426; 424/78.08; 424/78.37; 424/434; 424/457; 424/468; 424/486; 424/497; 525/450; 514/2
[58] Field of Search .................. 424/426, 78.08, 78.37, 424/434, 457, 468, 486, 497; 525/450; 514/2

[56] References Cited

U.S. PATENT DOCUMENTS

| | | | |
|---|---|---|---|
| 4,471,077 | 9/1984 | Lange | 521/56 |
| 4,622,244 | 11/1986 | Lapka | 427/213.32 |
| 4,652,441 | 3/1987 | Okada et al. | 424/19 |
| 4,675,189 | 6/1987 | Kent | 424/490 |
| 4,677,191 | 6/1987 | Tanaka et al. | 528/361 |
| 4,683,288 | 7/1987 | Tanaka et al. | 528/361 |
| 4,711,782 | 12/1987 | Okada et al. | 424/455 |
| 4,728,721 | 3/1988 | Yamamoto et al. | 528/361 |
| 4,767,628 | 8/1988 | Hutchinson | 424/426 |
| 4,849,228 | 7/1989 | Yamamoto et al. | 424/457 |
| 4,859,763 | 8/1989 | Takayanagi | 528/357 |
| 4,917,893 | 4/1990 | Okada et al. | 424/423 |
| 4,954,298 | 9/1990 | Yamamoto et al. | 264/4.6 |
| 4,962,091 | 10/1990 | Eppstein et al. | 514/2 |
| 5,061,492 | 10/1991 | Okada et al. | 424/423 |

FOREIGN PATENT DOCUMENTS

| | | |
|---|---|---|
| 0052510 | 11/1981 | European Pat. Off. . |
| 0190833 | 1/1986 | European Pat. Off. . |
| 0256726 | 7/1987 | European Pat. Off. . |
| 0263490 | 10/1987 | European Pat. Off. . |
| 0281482 | 3/1988 | European Pat. Off. . |
| 0350246 | 7/1989 | European Pat. Off. . |
| 2-212436 | 8/1990 | Japan . |

OTHER PUBLICATIONS

Chemical Abstracts, vol. 114/No. 6; (Feb. 11, 1991); Columbus, Ohio; Abstract No. 49615R.

*Primary Examiner*—G. S. Kishore
*Attorney, Agent, or Firm*—Wegner, Cantor, Mueller & Player

[57] ABSTRACT

A polymer for a prolonged release preparation which comprises
(A) a polylactic acid and
(B) a copolymer of glycolic acid and a hydroxycarboxylic acid of general formula

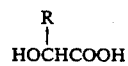

wherein R stands for an alkyl group having 2 to 8 carbons, wherein the weight ratio of (A) and (B) is in the range of 10/90 to 90/10. The drug is released at a constant rate from the preparation over the total release period without a large burst at the initial state. Furthermore, the drug release period of the preparation can be freely controlled by varying the blending ratio of (A) and (B).

17 Claims, No Drawings

PROLONGED RELEASE PREPARATION AND POLYMERS THEREOF

This application is a continuation of U.S. application Ser. No. 07/777,170, filed Oct. 16, 1991, now abandoned.

FIELD OF THE INVENTION

The present invention relates to a prolonged release preparation and polymers for said preparation.

BACKGROUND OF THE INVENTION

Biodegradable polymers can be used as bases for pharmaceutical preparations such as microcapsules. Such a biodegradable polymer is disclosed in Japanese Kokai Patent Application No. 61-28521 (the corresponding U.S. Pat. Nos. 4,677,191 and 4,683,288) which teaches that the polycondensation reaction of tactic acid and/or glycolic acid, in the presence or absence of a catalyst, gives rise to such a polymer or copolymer.

Japanese Patent publication No. 1-57087 (the corresponding U.S. Pat. Nos. 4,652,441, 4,711,782 and 4,917,893) discloses a method of manufacturing sustained-releasing microcapsules employing such biodegradable polymers.

Japanese Kokai Patent publication No. 62-54760 (the corresponding U.S. Pat. Nos. 4,728,721 and 4,849,228) mentions that the initial drug release Pattern of microcapsules can be improved by washing a biodegradable polymer solution with water to remove the water-soluble low molecular fraction.

Japanese Kokai Patent publication No. 2-212436 describes a prolonged release pharmaceutical polymer available on direct dehydrative polycondensation of lactic acid and/or glycolic acid with a hydroxycarboxylic acid.

In a prolonged release preparation comprising a dispersion of a drug substance in a biodegradable macromolecular compound, it is preferable that the rate of drug release can be controlled as desired. Generally the period of release of such a prolonged release preparation is controlled by adjusting the monomer composition and molecular weight of the biodegradable polymer used for the preparation. The rate of d-rug release is preferably constant over the entire period of release. As mentioned hereinbefore, many proposals have been made for improving the initial release Pattern of this type of preparation. However, when the designed release period is comparatively short, it is frequently encountered that the drug is released encased in the second half of the release period. Furthermore, the composition and molecular weight of the biodegradable polymer must be optimized for each drug used and each designed release period and this optimization requires much time and effort.

Furthermore, it is difficult to obtain a constant drug release Pattern by using a preparation mixing two kinds of microcapsule which have different release periods, since the drug release Pattern of the mixed preparation is apt to change discontinuously in the course of the drug release.

The inventors of the present invention explored into this field of technology for overcoming the above-mentioned disadvantages and found that when the period of drug release is controlled using a simple blend of a biodegradable polymer having a comparatively low degradation rate and a biodegradable polymer having a comparatively high degradation rate, the release characteristic of the system in the second half of the release period is remarkably improved over that of a system employing a copolymer of the same monomer composition. The present invention is predicated on the above finding.

SUMMARY OF THE INVENTION

The present invention is accordingly directed to (1) a polymer for a prolonged release preparation comprising a polylactic acid (A) and a copolymer (B) between glycolic acid and a hydroxycarboxylic acid of the formula (I)

wherein R means an alkyl group containing 2 to 8 carbon atoms as blended in a weight ratio of 10/90 through 90/10 and (2) a prolonged release preparation containing an effective amount of a water-soluble drug substance in said polymer (1).

DETAILED DESCRIPTION OF THE PREFERRED EMBODIMENT

The molecular weight in this specification means the polystyrene equivalent molecular weight as determined by gel permeation chromatography (GPC) using polystyrene as the reference standard. In the determination of molecular weights, the GPC column KF804L×2 (Shows Denko) and, as the mobile phase, chloroform were used.

The polylactic acid used in the present invention may be any of the L-, D- and D,L-polylactic acid but when a solvent is used in the formulation, the mole ratio of D- and L-lactic acid in the D, L-polylactic acid is usually 75/25 to 25/75, preferably 48/52 to 25/75, more preferably 45/55 to 25/75 from the standpoint of solubility. It is also preferably to use a polylactic acid which has a molecular weight peak value of 5000 to 30000 and shows, when used alone, a release period of about 2 to 4 months.

Two methods are known for the synthesis of said polylactic acid, namely the ring-opening polymerization of lactide which is a dimmer of lactic acid and the dehydrative polycondensation of lactic acid. For the preparation of a comparatively low molecular weight polymer for use in the present invention, the direct dehydrative polycondensation of lactic acid (cf. Japanese Kokai Patent Application No. 61-28521) is easier to carry out.

Referring to the copolymer (B), the constituent hydroxycarboxylic acid of general formula (I) includes, among others, 2-hydroxybutryic acid, 2-hydroxyvaleric acid, 2-hydroxy-3-methylburyric acid, 2-hydroxycaproic acid, 2-hydroxyisocaproic acid, 2-hydroxycaprylic acid and so on. Particularly preferred is 2-hydroxybutyric acid. These 2-hydroxycarboxylic acids may each be D-, L- or D,L-configured but the D,L compound is preferably used. The mode of copolymerization of the copolymer (B) may be random, block or graft. Among such glycolic acid copolymers, those which are degradated in the body with comparative rapidity and releases, when a preparation was made along, a water soluble drug within not longer than one month are preferred.

The preferred proportion of glycolic acid (I) in the copolymer (B) is in the range of 40 to 70 mole % of glycolic acid and the proportion of the hydroxycarboxylic acid is in the range of 60 to 30 mole %, respectively. If the proportion of glycolic acid is less than 40 mole %, the pattern of drug release may not be linear, while the use of more than 70 mole % of glycolic acid makes the copolymer hardly soluble in a solvent, thus making it difficult to manufacture the preparations. Moreover, the glycolic acid copolymer preferably has a molecular weight peak value of 5000 to 20000 as determined by GPC.

A method for synthesis of said glycolic acid copolymer (B) has been described for glycolic acid-L-leucinic acid copolymer in Japanese Kokai Patent Publication No. 2-212436. However, the copolymer (B) can be easily synthesized by the general synthetic methods. (e.g. Japanese Kokai Patent Application No. 61-28521).

In the pharmaceutical base according to the present invention, polylactic acid (A) and glycolic acid copolymer (B) can be used in a blend ratio of 10/90 through 90/10 (by weight), preferably 25/75 through 75/25 (by weight). If the proportion of either component is excessive, the resulting therapeutic system will have a release pattern not much different from the system exclusively composed of the one component and fail to show the desired linear second-half release characteristic. The method of blending is optional.

The biodegradable polymer composition thus obtained can be used as the pharmaceutical base for prolonged release preparations such as microcapsules.

The water-soluble drug substance which can be incorporated in the above preparations includes those substances which are highly hydrophilic and have low oil-water partition coefficients. The low oil-water partition coefficient means that the coefficient of partition between octanol and water, for instance, is not higher than about 0.1.

While the kinds of such water-soluble drug substances are virtually not limited, there may be employed a variety of physiologically active peptides, antibiotics, antitumor agents, antipyretics, analgesics, antiinflammatory agents, antitussive-experctrants, sedatives, muscle relaxants, antiepileptics, antiulcer agents, antidepressants, antiallergic agents, cardiotonics, antiarrhythmic agents, vasodilators, hypotensive diuretics, antidiabetic agents, anticoagulants, hemostatic agents, antituberculous agents, hormones, narcotic antagonists, bore resorption inhibitors, angiogenesis-inhibiting substances and so on.

The physiologically active peptide which is used in the present invention is one consisting of two or more amino acid residues and preferably has a molecular weight of about 200 to 80000.

As examples of such peptides there may be mentioned leutinizing hormone-releasing hormone (LH-RH) and its functional analogs such as the polypeptides of the formula

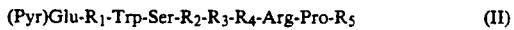

(Pyr)Glu-R$_1$-Trp-Ser-R$_2$-R$_3$-R$_4$-Arg-Pro-R$_5$     (II)

wherein R$_1$ means His, Tyr, Trp or p-NH$_2$-Phe; R$_2$ means Tyr or Phe; R$_3$ means Gly or a D-amino acid residue; R$_4$ means Leu, Ile or Nle; R$_5$ means Gly-NH-R$_6$ (R$_6$ is H or a lower alkyl group which may optionally have a hydroxyl group) or NH-R$_6$ (R$_6$ is as defined above) and salts thereof {cf. U.S. Pat. No. 3,853,837, U.S. Pat. No. 4,008,209 and U.S. Pat. No. 4,972,859, British Patent No. 1,423,083, Proceedings of the National Academy of Sciences of the U.S. of America 78, 6509–6512, 1981}.

Referring to the above formula (II), the D-amino acid residue R$_3$ includes, among others, α-D-amino acid residues containing up to 9 carbon atoms (e.g. D-Leu, Ile, Nle, Val, Nval, Abu, Phe, Phg, Ser, Thr, Met, Ala, Trp, α-Aibu, etc.), which may optionally have appropriate substituents (e.g. t-butyl, t-butoxy, t-butoxycarbonyl, etc.). Of course, acid salts and metal complex compounds of peptide (II) can likewise be employed.

Wherever, in this specification, abbreviations are used to indicate amino acids, peptides, protective groups, etc. in connection with the peptide of formula (II), they are either the abbreviations according to IUPAC-IUB Commission on Biological Nomenclature or those commonly used in this field of art. Furthermore, where any amino acid may exist as optical isomers, the L-isomer is meant unless it is specifically indicated otherwise.

A representative species is a polypeptide of formula (II) wherein R$_1$=His, R$_2$=Tyr, R$_3$=Tyr, R$_4$=Leu, R$_5$=NHCH$_2$—CH$_3$.

The polypeptide may also be any of LH-RH antagonist compounds (cf. U.S. Pat. No. 4,086,219, No. 4,124,577, No. 4,253,997, No. 4,317,815).

Among further examples of said peptide are insulin, somatostatin, somatostatin derivatives (U.S. Pat. No. 4,087,390, No. 4,093,574, No. 4,100,117, No. 4,253,998), growth hormone, prolactin, adrenocorticotropic hormone (ACTH), melanocyte stimulating hormone (MSH), thyrotropin-releasing hormone (TRH) and salts and derivatives thereof (Japanese Kokai Patent Application No. 50-121273 and No. 52-116465), thyroid-stimulating hormone (TSH), luteinizing hormone (LH), follicle-stimulating hormone (FSH), vasouressin, vasopressin derivatives [desmopressin, Folia Endocrinologica Japonica, 54, 5, 676-691 (1978)], oxytocin, calcitonin, parathyroid hormone, glucagon, gastrin, secretin, pancreozymine, cholecystokinin, angictensin, human placental lactogen, human chorionic gonadotropin (HCG), enkephalin, enkephalin derivatives [U.S. Pat. No. 4,277,394, European Patent Application Laid-open No. 315671, endorphin, kyotorphin, interferons ((α, β and γ), interieukins (I, II, III), taftsin, thymopoietinr thymosin, thymostimulin, thymic humoral factor (THF), thymic serum factor (FTS) as well as derivatives thereof (U.S. Pat. No. 4,229,438) and other thymic factors [Advances in Medicine 125, 10, 835–843 (1983)], tumor necrosis factor (TNF), colony-stimulating factor (CSF), motilin, dynorphin, bombesin, neurotensin, ceruiein, bradykinin, urokinase, asparaginase, kallikrein, substance p, nerve growth factor, blood-coagulation factor VIII, blood-coagulation factor IX, iysozyme chloride, polymyxin B, colistin, gramicidin, bacitracin, erythropoietin (EpO) and so on.

Among said antitumor agents may be bleomycin hydrochloride, methotrexate, actinomycin D, mitomycin C, vinblastine sulfate, vincristine sulfate, cisplatin, daunorubicin hydrochloride, adriamycin, neocarzinostatin, cytosine arabinoside, fluorouracil, tetrahydrofuryi-5-fluorouracil, krestin, picibanil, lentinan, levamisole, bestatin, azimexon, glycyrrhizin, poly I:C, poly A:U, poly ICLC and so on.

Among said antibiotics are gentamicin, dibekacin, kanendomycin, lividomycin, tobramycin, amikacin, fradiomycin, sisomicin, tetracycline hydrochloride, oxytetracycline hydrochloride, rolitetracycline, doxycycline hydrochloride, ampicillin, piperacillin, ticarcillin, cephalothin, cephaloridine, cefotiam, cefsuiodin, cefmenoxime, cefmetazole, cefazolin, cefotaxime, cefoperazone, ceftizoxime, moxalactam, thienamycin, sulfazeci-n, azthreonam and so on.

Among said antipyretics, analgesics and expectorants may be sodium salicylate, sulpyrine, sodium fllufenamate, diclofenac sodium, indomethacin sodium, morphine sulfate, pethidine hydrochloride, levorphanol tartrate, oxymorphone and so on. Among said antitussive-expectorants may be included ephedrine hydrochloride, methylephedrine hydrochloride, noscapine hydrochloride, codeine phosphate, dihydrocodeine phosphate, alloclamide hydrochloride, clofedanol hydrochloride, picoperidamine hydrochloride, cloperastine, protokylol hydrochloride, isoproterenol hydrochloride, salbutamol sulfate, terubutaline sulfate, etc. The sedatives may be chlorpromazine hydrochloride, prochlorperazine, trifluoperazine, atropine sulfate, methylscopoiamine bromide and so on. The muscle relaxants may be pridinoi methanesulfonate, tubocurarine chloride, pancuronium bromide and so on. The antiepileptics include sodium phenytoin, ethosuximide, acetazoiamide sodium, chlordiazepoxide hydrochloride and so on. The antiulcer agents include metoclopramide, histidine hydrochloride and so on. The antidepressants include imipramine, clomiparmine, noxiptiline, phenelzine sulfate and so on. The antiallergic agents include diphenhydramine hydrochloride, chlorpheniramine maleate, tripeiennamine hydrochloride, methdilazine hydrochloride, clemizoie hydrochloride, diphenylpyraline hydrochloride, methoxyphenamine hydrochloride and so on. The cardiotonics include trans-$\pi$-oxocamphor, theophyllol, aminophylline, etilefrine hydrochloride and so on. The antiarrhythmic agents include propranolol hydrochloride, alprenolol hydrochloride, bufetolol hydrochloride, oxprenolol hydrochlorde and so on. The vasodilators include oxyfedrine hydrochloride, diltiazem hydrochloride, tolazoline hydrochloride, hexobendine, bamethan sulfate and so on. The hypotensive diuretics include hexamethonium bromide, pentolinium, mecamylamine hydrochloride, ecarazine hydrochloride, clonidine hydrochloride and so on. The antidiabetic agents include glymidine sodium, glipizide, phenformin hydrochloride, buformine hydrochloride, metformin and so on, The anticoagulants include heparin sodium, sodium citrate and so on. The hemostatics include thromboplastin, thrombin, menadione sodium bisulfite, acetomenaphthone, $\gamma$-aminocaproic acid, tranexamic acid, carbazochrome sodium sulfonate, adrenochrome monoaminoguanidine methansulfonate and so on. The tuberculostats include isoniazid, ethambutol, sodium para-aminosalicylate and so on. The hormones include prednisolone succinate, prednisolone sodium phosphate, dexamethasone sodium sulfate, betamethasone sodium phosphate, hexestrol phosphate, hexestrol acetate, methimazoie and so on. The narcotic antagonists include levallorphan tartrate, nalorphine hydrochloride, naloxazone hydrochloride and so on. The bone resorption inhibitors include (sulfur-containing alkyl)aminomethylenebisphosphonic acid and so on. The angiogenesis-inhibiting substances include angiostatic steroid (Science, 221, 719 (1983)), fumagillin (e.g. EP-A-325199, etc.), fumagillol derivatives (e.g. EP-A-357061, EP-A-359036, EO-A-386667, EP-A-415294, etc.) and so on.

The proportion of said water-soluble drug depends on the kind of drug, expected phase acological effect and its duration etc. but its concentration in the inner aqueous phase of water in oil emulsion in the course of microencapsulation by in water drying process is selected from the range of about 0.001% to about 90% (w/w), preferably 0.01% to 80% (w/w).

The prolonged release preparation of the present invention can be manufactured by the per se known production technology (e.g. see U.S. Pat. No 4,652,441). An exemplary manufacturing process comprises preparing a W/O emulsion using an aqueous solution of the water-soluble drug as the inner aqueous phase, to which a drug retaining substance such as gelatin, albumin, pectin or agar is optionally added, and a solution of the prolonged release preparation of the present invention as the oil phase, dispersing said W/O emulsion in an aqueous medium to give a W/O/W emulsion and subjecting the latter to drying in water to give sustained-release microcapsules containing said water-soluble drug. Such microcapsules can also be manufactured by spray-drying the W/O emulsion.

Other forms of the prolonged release preparation than microcapsules can also be manufactured by melting an appropriate dispersion of the biodegradable composition and molding the melt into beads, rods, needles and other forms.

Dosage forms of administering microcapsules of the present invention include injections, implantations and agents absorbed through mucous membrane of rectum or uterus.

The microcapsules obtained in the above manner are sieved, when necessary after slightly crushing, to eliminate excessively large microcapsules. The average grain size of microcapsules is within the range from about 0.5 to 1000 $\mu$m, desirable and preferably within the range of about 2 to 500 $\mu$m. When the microcapsules are used as injections in the form of suspension, the grain size may be sufficient so long as it satisfies the requirements for dispersability and injectability, for example, desirably within the range of about 2 to 100 $\mu$m.

The microcapsules produced by the methods according to this invention have many advantages. For instance, they scarcely undergo aggregation or cohesion to one another during the production step. There can be obtained microcapsules which are satisfactorily spherical in shape having an optional size. The step of removing the solvent from the oil phase is easy to control, whereby the surface structure of microcapsules, which is decisive for the rate of drug release (inclusive, e.g. of the number and size of pores which are to serve as main routes of drug release), can be controlled.

The microcapsules produced by the method of this invention can be easily administered as injections and implants intramuscularly, subcutaneously, or at an organ, joint cavity or at a lesion such as tumors. They may also be administered in various dosage forms and thus can be used as materials in preparing such dosage forms.

For instance, in making up the microcapsules according to this invention for an injection, the microcapsules according to the invention are dispersed in an aqueous medium together with a dispersing agent (e.g. Tween 80, HCO-60, carboxymethylcellulose, sodium alginate, etc.), a preservative (e.g. methylparaben, propylparaben, etc.), an isotonizing agent (e.g. sodium chloride, mannitol, sorbitol, glucose, etc.), or suspended in an aqueous medium together with a vegetable oil such as sesame oil or corn oil. Such dispersion or suspension is formulated into a practically usable sustained-release injection.

Furthermore, the above microencapsulated sustained-release injection can be converted to a more stable, sustained-release injection by adding an additional excipient (e.g. mannitol, sorbitol, lactose, glucose, etc.), redispersing the resulting mixture and effecting solidification by freeze-drying or spray drying with extemuoraneous addition of distilled water for injection or some appropriate dispersing agent. The dose of the sustained-release preparation according to this invention may vary depending on the kind and amount of the water soluble drug, which is the active ingredient, dosage form, duration or drug release, recipient animal (e.g. warm-blooded animals such as mouse, rat, rabbit, sheep, pig, cow, horse, human) and purpose of administration but should be within the range of effective dose of said active ingredient. For example, the single dose per said animal of the microcapsules can adequately be selected within the range of about 0.1 mg to 100 mg/kg body weight, preferably about 0.2 mg to 50 mg/kg body weight.

EXAMPLE

The following comparative and working examples are intended to illustrate the present invention in further detail.

COMPARATIVE EXAMPLE 1

A 1000 ml four-necked flask equipped with nitrogen inlet and condenser lines was charged with 247.7 g of 90% aqueous D,L-lactic acid solution, 95.1 g of glycolic acid and 130.1 g of D,L-2-hydroxybutyric acid and the charge was heated in a nitrogen gas stream at 90° C. and 400 mm Hg to 150° C. and 30 mmHg over 5 hours to remove water as the distillate. The reaction mixture was further heated under reduced pressure at 150°–175° C. and 5–7 mmHg for 72 hours, at the end of which time it was cooled to give an amber-colored tactic acid-glycolic acid-2-hydroxybutyric acid copolymer.

This copolymer was dissolved in 1000 ml of dichloromethane and the solution was poured in warm water at 60° C. with stirring. The dough-like polymer precipitate was collected and dried in vacuo at 30° C.

The peak molecular weight (GPC) of the resulting lactic acid-glycolic acid-2-hydroxybutyric acid copolymer was 12000.

COMPARATIVE EXAMPLE 2

In 0.25 ml of distilled water was dissolved 350 mg of TRH (thyrotropin-releasing hormone) followed by addition of 4.65 g of the lactic acid-glycolic acid-2-hydroxybutyric acid copolymer obtained in Comparative Example 1 as dissolved in 5 ml of dichloromethane. The mixture was stirred with a small homogenizer for 60 seconds to give a W/O emulsion. This emulsion was cooled to 180° C. and poured into 1250 ml of a 0.15% aqueous solution of polyvinyl alcohol (PVA) preadjusted to 19° C. and the mixture was treated with a turbine homogenizer to give a W/O/W emulsion. Then, this W/O/W emulsion was stirred at room temperature to evaporate the dichloromethane and solidify the internal W/O emulsion which was collected by centrifugation. This product was dispersed again in distilled water and centrifuged to wash off the free drug and the like. The collected microcapsules were freeze-dried to give a powder. The result of an in vitro release test of the above microcapsules in phosphate buffer (pH 7.0) at 370° C. is shown in Table 1.

COMPARATIVE EXAMPLE 3

In 0.8 ml of distilled water were dissolved 450 mg of leuprorelin acetate (TAP-144) and 40 mg of gelatin and the solution was added to a solution of 4.5 g of the lactic acid-glycolic acid-2-hydroxybutyric acid copolymer obtained in Comparative Example 1 in 5 ml of dichloromethane. The mixture was treated with a compact homogenizer for 60 seconds to give a WIO emulsion. This emulsion was cooled to 18° C. and poured in 1200 ml of a 0.15% aqueous solution of polyvinyl alcohol (PVA) preadjusted to 20° C. and the mixture was treated with a turbine homomixer to give a W/O/W emulsion. Then, this W/O/W emulsion was stirred at room temperature to evaporate the dichloromethane and solidify the internal W/O emulsion, followed by centrifugation. This product was redispersed in distilled water and centrifuged again to wash off the free drug and the like.

The microcapsules thus obtained were freeze-dried to give a powder. The result of an in vitro release test of the above microcapsules in phosphate buffer (pH 7.0) at 37° C. is shown in Table 2.

COMPARATIVE EXAMPLE 4

A 1,000 ml four-necked flask equipped with nitrogen inlet and condenser means was charged with 247.7 g of 90% aqueous solution of DL-lactic acid and 190.2 g of glycolic acid and the charge was heated in a nitrogen gas stream under reduced pressure at 90° C./500° mmHg to 150° C./130 mmHg over 5 hours, with water being constantly distilled off. The reaction mixture was further heated under reduced pressure at 5–7 mmHg/150°–180° C. for 28 hours, after which it was cooled to give an amber-colored tactic acid-glycolic acid copolymer.

The copolymer thus obtained was dissolved in 1,000 ml of dichloromethane and the solution was poured in warm water at 600° C. with stirring. The resulting dough-like high polymer precipitate was collected and dried in vacuo at 300° C.

The peak molecular weight of the resulting lactic acid-glycolic acid copolymer as determined by GPC was 12,000.

COMPARATIVE EXAMPLE 5

In 0.8 ml of distilled water were dissolved 450 mg of leuprorelin acetate (TAP-144) and 40 mg of gelatin and the solution was added to a solution prepared by dissolving 4.5 g of a 1:1 mixture of the tactic acid-glycolic copolymer of Comparative Example 4 and the polylactic acid of Reference Example 1 in 5 ml of dichloromethane. The mixture was homogenized with a compact homogenizer for 60 seconds to give a WIO emulsion. This emulsion had the tendency to separate into two layers. This emulsion was cooled to 18° C. and poured in 1,200 ml of 0.15% aqueous solution of polyvinyl alcohol (PVA) preadjusted to 200° C. The mixture was homogenized with a turbine homomixer to give a W/O/W emulsion. Then, while this W/O/W emulsion was stirred at room temperature, the dichloromethane was evaporated to solidify the internal W/O emulsion which was then collected by centrifugation. This emulsion was redispersed in distilled water and further centrifuged to wash out the free drug, etc.

The collected microcapsules were lyophilized to give a powder. The result of the in vitro release test of the microcapsules in phosphate buffer (pH 7.0) at 370° C. is shown in Table 2.

REFERENCE EXAMPLE 1

A 1000 ml four-necked flask equipped with nitrogen inlet and condenser lines was charged with 495.4 g of a 90% aqueous solution of D,L-lactic acid and the charge was heated under reduced pressure in a nitrogen gas stream at 900° C. and 400 mmHg ~1500° C. and 30 mmHg over 5 hours to remove water as the distillate. The reaction mixture was further heated under reduced pressure at 5-7 mmHg and 150°~1750° C. for 65 hours and, then, cooled to give an amber-colored Dolylactic acid.

This polymer was dissolved in 1000 ml of dichloromethane and added to warm water at 600° C. with stirring. The doughy polymer precipitate was collected and dried in vacuo at 300° C.

The peak molecular weight of the resulting polylactic acid as determined by GPC was 16000.

REFERENCE EXAMPLE 2

A 1000 ml four-necked flask equipped with nitrogen inlet and condenser lines was charged with 190.2 g of glycolic acid and 260.2 g of D,L-2-hydroxybutyric acid and the charge was heated under reduced pressure in a nitrogen gas stream at 90° C. and 400 mmHg ~1500° C. and 30 mmHg over 5 hours to remove water as the distillate. The reaction mixture was further heated under reduced pressure at 5-7 mmHg and 150°-175° C. for 72 hours and, then, cooled to give an amber-colored glycolic acid-2-hydroxybutyric acid copolymer.

This copolymer was dissolved in 1000 ml of dichloromethane and added to warm water at 60° C. with stirring. The doughy polymer precipitate was collected and dried in vacuo at 300° C.

The peak molecular weight of this glycolic acid-2-hydroxybutyric acid copolymer as determined by GPC was 10000.

REFERENCE EXAMPLE 3

A 1,000 ml four-necked flask equipped with nitrogen inlet and condenser means was charged with 300 g of 90% aqueous solution of D,L-lactic acid and 100 g of 90% L-lactic acid and the charge was heated in a nitrogen gas stream under reduced pressure at 100° C./500° mmHg to 150° C./30 mmHg over 4 hours, with water being constantly distilled off. The reaction mixture was heated under reduced pressure at 5-7 MmHg/150°-180° C. for 24 hours, after which it was cooled to give an amber-colored lactic acid polymer.

This polymer was dissolved in 1,000 ml of dichloromethane and the solution was poured in warm water at 60° C. with stirring. The dough-like polymer precipitate was collected and dried in vacuo at 300° C.

As determined by GPC, the peak molecular weight value of this lactic acid polymer was 7,000.

REFERENCE EXAMPLE 4

A 1,000 ml four-necked flask equipped with nitrogen inlet and condenser means was charged with 145.8 g of D,L-2-hydroxybutyric acid and 177.7 g of glycolic acid and the charge was heated in a nitrogen gas stream under reduced pressure at 10° C./500 mmHg to 150° C./30 mmHg over 3.5 hours, with water being constantly distilled off. The reaction mixture was further heated under reduced pressure at 5-7 mmHg/150°-180° C. for 27 hours, followed by cooling to give an amber-colored glycolic acid-2-hydroxybutyric acid copolymer.

This copolymer was dissolved in 1,000 ml of dichloromethane and the solution was poured in warm water at 600° C. with stirring. The resulting dough-like polymer precipitate was collected and dried in vacuo at 250° C.

As determined by GPC, the peak molecular weight value of this glycolic acid-2-hydroxybutyric acid copolymer was 14,000.

EXAMPLE 1

Using a 3:1 (w/w) mixture of the polylactic acid prepared in Reference Example 1 and the glycolic acid-2-hydroxybutyric acid copolymer prepared in Reference Example 1, the procedure of Comparative Example 2 was followed to prepare microcapsules. The result of an in vitro release test of the above microcapsules in phosphate buffer (pH 7.0) at 370° C. is shown in Table 1.

EXAMPLE 2

Using a 1:1 (w/w) mixture of the polylactic acid prepared in Reference Example 1 and the glycolic acid-2-hydroxybutyric acid copolymer prepared in Reference Example 2, the procedure of Comparative Example 2 was followed to prepare microcapsules. The result of an in vitro release test of the above microcapsules in phosphate buffer (pH 7.0) at 37° C. is shown in Table 1.

EXAMPLE 3

Using a 1:3 (w/w) mixture of the polylactic acid prepared in Reference Example 1 and the glycolic acid-2-hydroxybutyric acid copolymer obtained in Reference Example 2, the procedure of Comparative Example 2 was followed to prepare microcapsules. The result of an in vitro release test of the above microcapsules in phosphate buffer (pH 7.0) at 370° C. is shown in Table 1.

TABLE 1

|  | Percent residue of TRH, (%)[a] | | | | | | |
| --- | --- | --- | --- | --- | --- | --- | --- |
|  | One day | One week | Two weeks | Three weeks | Four weeks | Five weeks | Six weeks |
| Comparative Example 2 | 95.1 | 79.8 | 50.1 | 2.9 | | | |
| Example 1 | 97.0 | 86.8 | 70.2 | 52.1 | 34.8 | 16.2 | 0.7 |
| Example 2 | 95.7 | 76.8 | 52.0 | 24.3 | 3.1 | | |
| Example 3 | 93.3 | 62.0 | 21.7 | 0.1 | | | |

[a] 1/30 M phosphate buffer, pH 7.0, 37° C.

It is apparent from Table 1 that the release period can be adjusted to 6, 4 and 3 weeks, respectively, by varying the blending ratio between polylactic acid (A) and glycolic acid-2-hydroxybutyric acid copolymer (B). Furthermore, whereas the microcapsules of Comparative Example 2 cannot release the drug at constant rate, all the microcapsules of the invention can release the drug at substantially constant rate.

EXAMPLE 4

Using a 3:1 (w/w) mixture of the polylactic acid prepared in Reference Example 1 and the glycolic acid-2-hydroxybutyric acid copolymer prepared in Reference Example 2, the procedure of Comparative Example 3 was followed to prepare microcapsules. The result of an in vitro release test of these microcapsules in phosphate buffer (pH 7.0) at 37° C. is shown in Table 2.

EXAMPLE 5

Using a 1:1 mixture of the polylactic acid prepared in Reference Example 1 and the glycolic acid-2-hydroxybutyric acid copolymer prepared in Reference Example 2, the procedure of Comparative Example 3 ,7 as followed to prepare microcapsules. The result of an in vitro release test cf the above microcapsules in phosphate buffer (pH 7.0) at 37° C. is shown in Table 2.

EXAMPLE 6

Using a 1:3 (w/w) mixture of the polylactic acid prepared in Reference Example 1 and the glycolic acid-2-hydroxybutyric acid copolymer prepared in Reference Example 2, the procedure of Comparative Example 3 was followed to prepare microcapsules. The result of an in vitro release test of these microcapsules in phosphate buffer (pH 7.0) at 37° C. is shown in Table 2.

TABLE 2

| | Percent residue of TAP-144 (%)[a] | | | | | |
|---|---|---|---|---|---|---|
| | One day | One week | Two weeks | Three weeks | Four weeks | Five weeks | Six weeks |
| Comparative Example 3 | 93.8 | 76.2 | 57.1 | 19.5 | 0.1 | | |
| Comparative Example 5 | 50.7 | 41.7 | 23.8 | 11.7 | 5.4 | 3.4 | |
| Example 4 | 97.2 | 88.1 | 72.3 | 56.1 | 38.4 | 23.7 | 6.0 |
| Example 5 | 96.1 | 77.8 | 56.0 | 36.8 | 15.0 | 0.1 | |
| Example 6 | 94.1 | 60.6 | 24.3 | 0.1 | | | |

[a] 1/30 M phosphate buffer, pH 7.0, 37° C.

It is apparent from Table 2 that the release period can be adjusted to the desirous period by varying the blending ratio of polylactic acid (A) to glycolic acid-2-hydroxybutyric acid copolymer (B). Whereas the drug release rate from the microcapsules of Comparative Example 3 was not constant, all the microcapsules of the present invention can release the drug at a substantially constant rate over the entire period. As shown for Comparative example 5, the combination of polylactic acid (A) and lactic acid-glycolic acid copolymer (B) did not achieve the effect of the invention.

EXAMPLE 7

In 0.4 ml of distilled water was dissolved 400 mg of leuprorelin acetate (TAP-144) and the solution was added to a solution prepared by dissolving 4.0 g of a 1:1 mixture of the polylactic acid of Reference Example 3 and the glycolic acid-2-hydroxybutyric acid copolymer of Reference Example 4 in 5 ml of dichloromethane. The mixture was homogenized with a compact homogenizer for 60 seconds to give a W/O emulsion. This emulsion was cooled to 18° C. and poured in 1,000 ml of a 0.1% aqueous solution of polyvinyl alcohol (PVA) preadjusted to 20° C. The mixture was homogenized with a turbine homomixer to give a W/O/W emulsion. The, while this W/O/W emulsion was stirred at room temperature, the dichloromethane was evaporated to solidify the internal W/O emulsion which was then collected by centrifugation. This emulsion was redispersed in distilled water and further centrifuged to wash out the free drug, etc.

The collected microcapsules were lyophilized to give a powder. The result of the in vitro release test of the microcapsules in phosphate buffer (pH 7.0 ) at 37° C. is shown in Table 3.

TABLE 3

| | Percent reside of TAP-144 (%)[a] | | | | | |
|---|---|---|---|---|---|---|
| | One day | One week | Two weeks | Three weeks | Four weeks | Five weeks |
| Example 7 | 91.1 | 60.1 | 29.1 | 9.3 | 1.8 | 0.2 |

[a] 1/30 M phosphate buffer, pH 7.0, 37° C.

When a prolonged release therapeutic system is manufactured using the prolonged release phase ascetical base comprising a blend of a polylactic acid and a glycolic acid copolymer in accordance with the present invention, the drug release period of the therapeutic system can be freely controlled by varying the blending ratio. Furthermore, the drug is released at a constant rate over the total release period without a large burst at the initial stage.

What is claimed is:

1. A polymer composition for a prolonged release preparation which comprises
   (A) a polylactic acid having a molecular weight peak value between 5,000 to 30,000 Daltons as determined by Gel Permeation Chromatography and
   (B) a copolymer having a molecular weight peak value between 5,000 to 20,000 Daltons as determined by Gel Permeation Chromatography of 40 to 70 mole % glycolic acid and 60 to 30 mole % of hydroxycarboxylic acid of the formula

wherein R stands for an alkyl group having 2 to 8 carbons, wherein the weight ration of (A) and (B) is in the range of 10/90 through 90/10.

2. The polymer composition according to claim 1, wherein the polylactic acid is a polymer of D-lactic acid and L-lactic acid.

3. The polymer composition according to claim 1, wherein the polylactic acid is a polymer of D-lactic acid and L-lactic acid, and the mole ratio of D- and L-lactic acid is 45/55 to 25/75.

4. The polymer composition according to claim 1, wherein the hydroxycarboxylic acid is a member selected from the group consisting of 2-hydroxybutryic acid, 2-hydroxyvaleric acid, 2-hydroxy-3-methylburyric acid, 2-hydroxycaproic acid, 2-hydroxyisocaproic acid and 2-hydroxycaprylic acid.

5. A method of producing a polymer composition for a prolonged release preparation which comprises mixing
   (A) a polylactic acid having a molecular weight peak value between 5,000 to 30,000 Daltons as determined by Gel Permeation Chromatography and
   (B) a copolymer having a molecular weight peak value between 5,000 to 20,000 Daltons as determined by Gel Permeation Chromatography of 40 to 70 mole % glycolic acid and 60 and 30 moist of a hydroxycarboxylic acid of the formula

where R stands for an alkyl group having 2 to 8 carbons, wherein the weight ratio of (A) and (B) is in the range of 10/90 through 90/10.

6. The method according to claim 5, wherein the polylactic acid is a polymer of D-lactic acid and L-lactic acid.

7. The method according to claim 5, wherein the polylactic acid is a polymer of D-lactic acid and L-lactic acid, and the mole ratio of D- and L-lactic acid is 45/55 to 25/75.

8. The method according to claim 5, wherein the hydroxycarboxylic acid is a member selected from the group consisting of 2-hydroxybutyric acid, 2-hydroxyvaleric acid, 2-hydroxy-3-methylbutylic acid, 2-hydroxycaproic acid, 2-hydroxyisocaproic acid and 2-hydroxycaprylic acid.

9. A prolonged release preparation which comprises a water-soluble drug being dispersed in a polymer composition for a prolonged release preparation comprising
    (A) a polylactic acid having a molecular weight peak value between 5,000 to 30,000 Daltons as determined by Gel Permeation Chromatography and
    (B) a copolymer having a molecular weight peak value between 5,000 to 20,000 Daltons as determined by Gel Permeation Chromatography of 40 to 70 mole % glycolic acid and 60 to 30 mole % of a hydroxycarboxylic acid of the formula

wherein R stands for an alkyl group having 2 to 8 carbons, wherein the weight ratio of (A) and (B) is in the range of 10/90 through 90/10.

10. The prolonged release preparation according to claim 9, wherein the polylactic acid is a polymer of D-lactic acid and L-lactic acid.

11. The prolonged release preparation according to claim 9, wherein the polylactic acid is a polymer of D-lactic acid and L-lactic acid, the mole ratio of D- and L-lactic acid is 45/55 to 25/75.

12. The prolonged release preparation according to claim 9, wherein the hydroxycarboxylic acid is a member selected from the group consisting of 2-hydroxybutyric acid, 2-hydroxyvaleric acid, 2-hydroxy-3-methylbutylic acid, 2-hydroxycaproic acid, 2-hydroxyisocaproic acid and 2-hydroxycaproic acid.

13. The prolonged release preparation according to claim 9, wherein the water-soluble drug is a physiologically active polypeptide.

14. The prolonged release preparation according to claim 13, wherein the physiologically active polypeptide is leutinizing hormone-releasing hormone or its functional analogs.

15. The prolonged release preparation according to claim 14, wherein the functional analogs of leutinizing hormone-releasing hormone are compounds of the formula

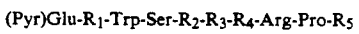

wherein $R_1$ means His, Tyr, Trp or p-$NH_2$-Phe; $R_2$ means Tyr or Phe; $R_3$ means Gly or a D-amino acid residue; $R_4$ means Leu, Ile or Nle; $R_5$ means Gly-NH-$R_6$ ($R_6$ is H or a lower alkyl group which may optionally have hydroxyl group) or NH-$R_6$ ($R_6$ is as defined above) or salts thereof.

16. The prolonged release preparation according to claim 13, wherein the physiologically active polypeptide is (Pyr)Glu-His-Trp-Ser-Tyr-D-Leu-Leu-Arg-Pro-NH-$C_2H_5$ or acetate thereof.

17. A prolonged release preparation according to claim 9 wherein the water-soluble drug is selected from the group consisting of physiologically active peptides, antibiotics, antitumor agents, antipyretics, analgesics, antiinflammatory agents, antitussiveexpectorants, sedatives, muscle relaxants, antiepileptics, antiulcer agents, antidepressants, antiallergic agents, cardiotonics, antiarrhythmic agents, vasodilators, hypotensive diuretics, antidiabetic agents, anticoagulants, hemostatic agents, antituberculous agents, hormones, narcotic antagonists, bone resorption inhibitors, and angiogenesis inhibiting substances.

* * * * *